(12) United States Patent
Bae et al.

(10) Patent No.: US 12,663,424 B2
(45) Date of Patent: Jun. 23, 2026

(54) ANTIBODY SPECIFICALLY BINDING TO WRS PROTEIN, AND USE THEREOF

(71) Applicant: JW BIOSCIENCE, Chungcheongbuk-do (KR)

(72) Inventors: Sumi Bae, Chungcheongbuk-do (KR); Sunghwa Son, Chungcheongbuk-do (KR); Yunsun Kim, Chungcheongbuk-do (KR); Jieun Park, Chungcheongbuk-do (KR); Min Chul Park, Gyeonggi-do (KR); Su Jin Kang, Gyeonggi-do (KR)

(73) Assignee: JW BIOSCIENCE, Chungcheongbuk-Do (KR)

( * ) Notice: Subject to any disclaimer, the term of this patent is extended or adjusted under 35 U.S.C. 154(b) by 1194 days.

(21) Appl. No.: 17/628,022

(22) PCT Filed: Jul. 17, 2020

(86) PCT No.: PCT/KR2020/009477
§ 371 (c)(1),
(2) Date: Jan. 18, 2022

(87) PCT Pub. No.: WO2021/010800
PCT Pub. Date: Jan. 21, 2021

(65) Prior Publication Data
US 2022/0268787 A1 Aug. 25, 2022

(30) Foreign Application Priority Data
Jul. 18, 2019 (KR) ........................ 10-2019-0087233

(51) Int. Cl.
*C07K 16/40* (2006.01)
*G01N 33/575* (2026.01)
*G01N 33/68* (2006.01)

(52) U.S. Cl.
CPC ......... *G01N 33/6893* (2013.01); *C07K 16/40* (2013.01); *G01N 33/575* (2026.01);
(Continued)

(58) Field of Classification Search
CPC ............ G01N 33/6893; G01N 33/574; G01N 2333/9015; G01N 2800/26;
(Continued)

(56) References Cited

U.S. PATENT DOCUMENTS 4,737,456 A 4/1988 Weng et al.
4,816,567 A 3/1989 Cabilly et al.
(Continued)

FOREIGN PATENT DOCUMENTS

CN 110603055 A 12/2019
CN 115335408 A 11/2022
(Continued)

OTHER PUBLICATIONS

Goel et al. "Plasticity within the Antigen Combining Site May Manifest as Molecular Mimicry in the Humoral Immune Response," The Journal of Immunology (2004), 173(12):7358-7367. (Year: 2004).*

(Continued)

*Primary Examiner* — Christopher L Chin
*Assistant Examiner* — Ellis Follett Lusi
(74) *Attorney, Agent, or Firm* — HULTQUIST, PLLC; Steven J. Hultquist

(57) ABSTRACT

The present invention relates to an antibody specifically binding to a tryptophanyl-tRNA synthetase (WRS) protein and, more specifically, to: an antibody, or a fragment of the antibody, specifically binding to a polypeptide of an amino acid sequence represented by SEQ ID NO: 2 in a WRS (Continued)

protein; a polynucleotide encoding the antibody and a vector comprising same; a cell transformed using same; and a use thereof.

7 Claims, 6 Drawing Sheets

Specification includes a Sequence Listing.

(52) U.S. Cl.
  CPC . *G01N 2333/9015* (2013.01); *G01N 2800/26* (2013.01); *G01N 2800/7095* (2013.01)

(58) Field of Classification Search
  CPC ... G01N 2800/7095; G01N 2800/7028; G01N 33/573; G01N 33/57488; G01N 33/577; C07K 16/40; C07K 2317/33; C07K 2317/34; C07K 2317/92; C07K 2317/56; C07K 2317/565
  USPC ............. 435/7.1; 530/388.1, 388.15, 388.25, 530/388.23, 387.1, 388.2, 388.26
  See application file for complete search history.

(56)                 References Cited

U.S. PATENT DOCUMENTS

| 5,565,332 | A  | 10/1996 | Hoogenboom et al. |
| 5,573,905 | A  | 11/1996 | Lerner et al. |
| 2002/0182666 | A1 | 12/2002 | Schimmel et al. |
| 2006/0078556 | A1 | 4/2006 | Glidden |
| 2010/0158883 | A1 | 6/2010 | Schimmel et al. |
| 2013/0330312 | A1 | 12/2013 | Greene et al. |
| 2014/0127183 | A1 | 5/2014 | Schimmel et al. |

FOREIGN PATENT DOCUMENTS

| EP | 2107375 | A1 | 10/2009 |
| JP | 2008-508349 | A | 3/2008 |
| JP | 2018-527590 | A | 9/2018 |
| KR | 1020150077891 | A | 7/2015 |
| KR | 1020170027313 | A | 3/2017 |
| WO | 0175078 | A1 | 10/2001 |

OTHER PUBLICATIONS

Lloyd et al. "Modelling the human immune response: performance of a 1011 human antibody repertoire against a broad panel of therapeutically relevant antigens," Protein Engineering, Design & Selection (2009), 22(3):159-168 (Year: 2009).*

Edwards et al. The remarkable flexibility of the human antibody repertoire; isolation of over one thousand different antibodies to a single protein, BlyS, Journal of Molecular Biology (2003), 334:103-118 (Year: 2003).*

EESR issued in European Patent Application No. 20841295.7 on Jul. 17, 2023.

Hjelm, B., et al., "Exploring epitopes of antibodies toward the human tryptophanyl-tRNA synthetase", New Biotechnology, 2009, pp. 129-137, vol. 27, No. 2, Publisher: Elsevier.

Notice of Allowance in counterpart Korean Patent Application 10-2020-0089014 issued on Sep. 26, 2022.

English Translation of Notice of Allowance in counterpart Korean Patent Application 10-2020-0089014 issued on Sep. 26, 2022.

Office Action issued in counterpart Japanese Patent Application No. 2022-503816 on Feb. 20, 2023.

English Translation of Office Action issued in counterpart Japanese Patent Application No. 2022-503816 on Feb. 20, 2023.

Lee, C-W, et al., "Overexpressed tryptophyanyl-tRNA synthetase, an angiostatic protein, enhances oral cancer cell invasiveness", Oncotarget, 2015, pp. 21979-21992, vol. 6, No. 26.

Chen, X., "Studies on the structure and function of tryptophanyl-tRNA synthetase", Doctoral Dissertation, Graduate School of Chinese Academy of Sciences, 2007, English Translation.

Office Action issued on Jun. 28, 2024 for Chinese Patent Application 202080065087.4.

English Translation of Office Action issued on Jun. 28, 2024 for Chinese Patent Application 202080065087.4.

Search Report issued on Jun. 25, 2024 for Chinese Patent Application 202080065087.4.

Paley, E.L., "Chaperon-like Activation of Serum-Inducible Tryptophanyl-tRNA Synthetase Phosphorylation through Refolding as a Tool for Analysis of Clinical Samples", Translational Oncology, 2011, pp. 377-389, vol. 4, No. 6, Publisher: Neoplasia Press, Inc.

Clackson, T., et al., "Making antibody fragments using phage display libraries", Nature, 1991, pp. 624-628, vol. 352.

Ghanipour, A., et al., "The Prognostic Significance of Tryptophanyl-tRNA Synthetase in Colorectal Cancer", Cancer Epidemiol Biomarkers Prev., 2009, pp. 2949-2955, vol. 18, No. 11.

Griffiths, A.D., et al., "Human anti-self antibodies with high specificity from phage display libraries", The EMBO Journal, 1993, pp. 725-734, vol. 12, No. 2.

Johnson, K.S., et al., "Human antibody engineering", Current Opinion in Structural Biology, 1993, pp. 564-571, vol. 3.

Kholer, et al., "Continuous cultures of fused cells secreting antibody of predefined specificity", Nature, 1975, pp. 495-497, vol. 256, Publisher: Nature Publishing Group.

Marks, J.D., et al., "By-passing Immunization Human Antibodies from V-gene Libraries Displayed on Phage", J. Mol. Biol., 1991, pp. 581-597, vol. 222, Publisher: Academic Press Limited.

Morrison, S.L., et al., "Chimeric human antibody molecules: Mouse antigen-binding domains with human constant region domains", Proc. Natl. Acad. Sci. USA, 1984, pp. 6851-6855, vol. 81.

O'sullivan, M.J., et al., "Methods for the Preparation of Enzyme-Antibody Conjugates for Use in Enzyme Immunoassay", Methods in Enzymology, 1981, pp. 147-166, vol. 73, Publisher: Academic Press, Inc.

Presta, L.G., "Selection, design, and engineering of therapeutic antibodies", J. Allergy Clin. Immunol., 2005, pp. 731-736, vol. 116, Publisher: American Academ of Allergy, Asthma and Immunology.

* cited by examiner

【FIG. 1】

Polynucleotide sequence encoding light-chain variable region (384 bp)

Leader sequence-FR1-CDR1-FR2-CDR2-FR3-CDR3-FR4

Light-chain variable region amino acid sequence (128 aa)

Leader sequence-FR1-CDR1-FR2-CDR2-FR3-CDR3-FR4

Polynucleotide sequence encoding heavy-chain variable region (414 bp)

Leader sequence-FR1-CDR1-FR2-CDR2-FR3-CDR3-FR4

Heavy-chain variable region amino acid sequence (138 aa)

Leader sequence-FR1-CDR1-FR2-CDR2-FR3-CDR3-FR4

【FIG. 2】
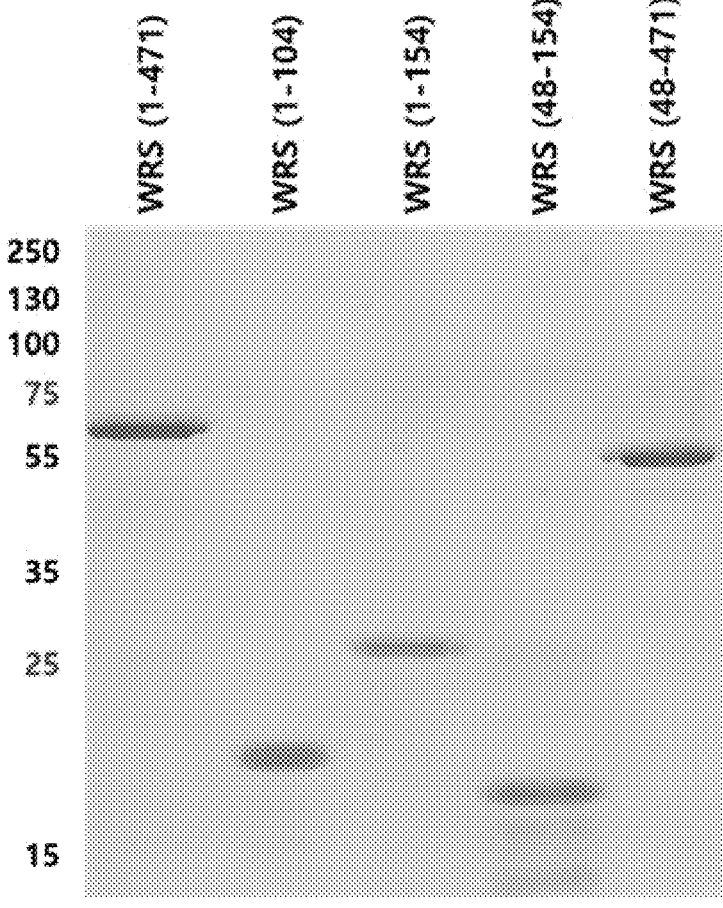

【FIG. 3】
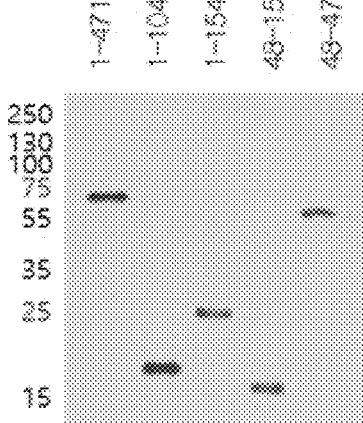

【FIG. 4】
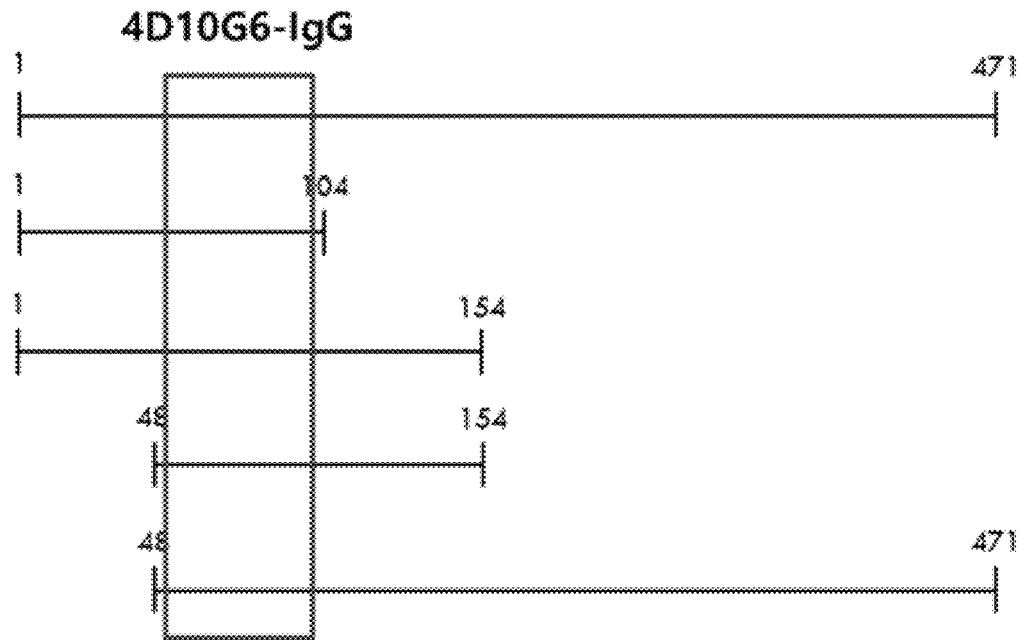

【FIG. 5】
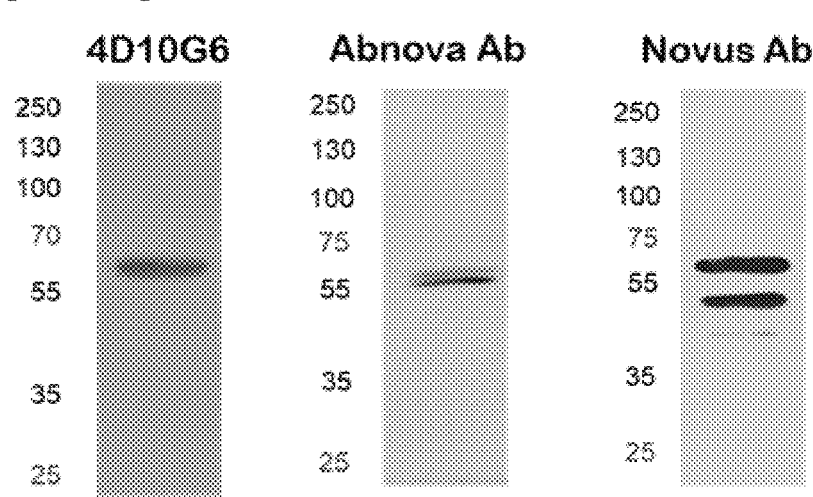

【FIG. 6】
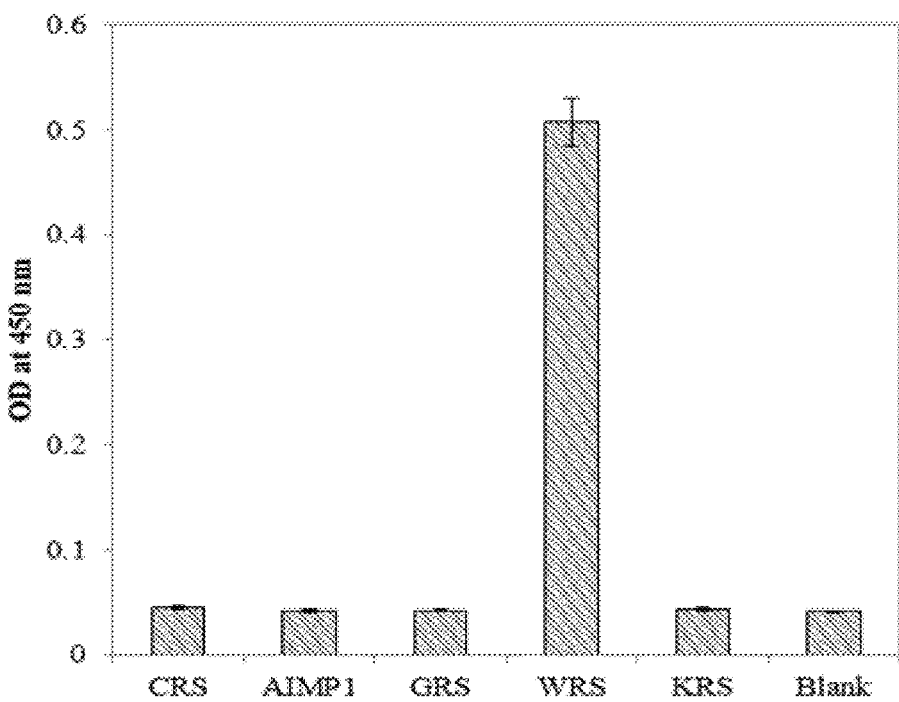

SEQUENCE LISTING

<160> NUMBER OF SEQ ID NOS: 10

<210> SEQ ID NO 1
<211> LENGTH: 471
<212> TYPE: PRT
<213> ORGANISM: Artificial Sequence
<220> FEATURE:
<223> OTHER INFORMATION: human tryptophanyl-tRNA synthetase(WRS) full
     length

<400> SEQUENCE: 1

```
Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
        195                 200                 205

Asp Gln Ala Tyr Ser Tyr Ala Val Glu Asn Ala Lys Asp Ile Ile Ala
    210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
            260                 265                 270

Asp Cys Ile Gly Lys Ile Ser Phe Pro Ala Ile Gln Ala Ala Pro Ser
        275                 280                 285

Phe Ser Asn Ser Phe Pro Gln Ile Phe Arg Asp Arg Thr Asp Ile Gln
    290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
        355                 360                 365

Lys Thr Lys Val Asn Lys His Ala Phe Ser Gly Gly Arg Asp Thr Ile
    370                 375                 380

Glu Glu His Arg Gln Phe Gly Gly Asn Cys Asp Val Asp Val Ser Phe
```

-continued

```
385                 390                 395                 400

Met Tyr Leu Thr Phe Phe Leu Glu Asp Asp Asp Lys Leu Glu Gln Ile
                405                 410                 415

Arg Lys Asp Tyr Thr Ser Gly Ala Met Leu Thr Gly Glu Leu Lys Lys
                420                 425                 430

Ala Leu Ile Glu Val Leu Gln Pro Leu Ile Ala Glu His Gln Ala Arg
            435                 440                 445

Arg Lys Glu Val Thr Asp Glu Ile Val Lys Glu Phe Met Thr Pro Arg
    450                 455                 460

Lys Leu Ser Phe Asp Phe Gln
465                 470
```

```
<210> SEQ ID NO 2
<211> LENGTH: 57
<212> TYPE: PRT
<213> ORGANISM: Artificial Sequence
<220> FEATURE:
<223> OTHER INFORMATION: Peptide fragment of human tryptophanyl-tRNA
      synthetase

<400> SEQUENCE: 2

Met Ser Tyr Lys Ala Ala Ala Gly Glu Asp Tyr Lys Ala Asp Cys Pro
1               5                   10                  15

Pro Gly Asn Pro Ala Pro Thr Ser Asn His Gly Pro Asp Ala Thr Glu
                20                  25                  30

Ala Glu Glu Asp Phe Val Asp Pro Trp Thr Val Gln Thr Ser Ser Ala
            35                  40                  45

Lys Gly Ile Asp Tyr Asp Lys Leu Ile
    50                  55
```

```
<210> SEQ ID NO 3
<211> LENGTH: 14
<212> TYPE: PRT
<213> ORGANISM: Artificial Sequence
<220> FEATURE:
<223> OTHER INFORMATION: Light chain CDR1 of anti-WRS monoclonal
      antibody

<400> SEQUENCE: 3

Arg Ser Ser Thr Gly Ala Val Thr Thr Ser Asn Tyr Ala Asn
1               5                   10
```

```
<210> SEQ ID NO 4
<211> LENGTH: 7
<212> TYPE: PRT
<213> ORGANISM: Artificial Sequence
<220> FEATURE:
<223> OTHER INFORMATION: Light chain CDR2 of anti-WRS monoclonal
      antibody

<400> SEQUENCE: 4

Gly Thr Asn Asn Arg Ala Pro
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Light chain CDR3 of anti-WRS monoclonal
      antibody

<400> SEQUENCE: 5
```

```
Val Leu Trp Tyr Ser Asn His Trp Val
1               5

<210> SEQ ID NO 6
<211> LENGTH: 5
<212> TYPE: PRT
<213> ORGANISM: Artificial Sequence
<220> FEATURE:
<223> OTHER INFORMATION: Heavy chain CDR1 of anti-WRS monoclonal
      antibody

<400> SEQUENCE: 6

Asp Tyr Asn Met Asn
1               5

<210> SEQ ID NO 7
<211> LENGTH: 17
<212> TYPE: PRT
<213> ORGANISM: Artificial Sequence
<220> FEATURE:
<223> OTHER INFORMATION: Heavy chain CDR2 of anti-WRS monoclonal
      antibody

<400> SEQUENCE: 7

Val Ile Asn Pro Asn Tyr Gly Thr Ile Arg Tyr Asn Gln Lys Phe Lys
1               5                  10                  15

Gly

<210> SEQ ID NO 8
<211> LENGTH: 10
<212> TYPE: PRT
<213> ORGANISM: Artificial Sequence
<220> FEATURE:
<223> OTHER INFORMATION: Heavy chain CDR3 of anti-WRS monoclonal
      antibody

<400> SEQUENCE: 8

Leu Leu Arg Gly Tyr Tyr Ala Met Asp Tyr
1               5                  10

<210> SEQ ID NO 9
<211> LENGTH: 128
<212> TYPE: PRT
<213> ORGANISM: Artificial Sequence
<220> FEATURE:
<223> OTHER INFORMATION: Light chain variable region of anti-WRS
      monoclonal antibody

<400> SEQUENCE: 9

Met Ala Trp Ile Ser Leu Ile Leu Ser Leu Leu Ala Leu Ser Ser Gly
1               5                  10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Val Leu Trp
            100                 105                 110
```

-continued

```
Tyr Ser Asn His Trp Val Phe Gly Gly Gly Thr Lys Leu Thr Val Leu
        115                 120                 125

<210> SEQ ID NO 10
<211> LENGTH: 138
<212> TYPE: PRT
<213> ORGANISM: Artificial Sequence
<220> FEATURE:
<223> OTHER INFORMATION: Heavy chain variable region of anti-WRS
      monoclonal antibody

<400> SEQUENCE: 10

Met Gly Trp Ser Trp Ile Phe Leu Leu Leu Leu Ser Gly Thr Ala Gly
1               5                   10                  15

Val His Ser Glu Phe Gln Leu Gln Gln Ser Gly Pro Glu Leu Val Lys
            20                  25                  30

Pro Gly Ala Ser Val Lys Ile Ser Cys Lys Ala Ser Gly Tyr Ala Phe
        35                  40                  45

Ile Asp Tyr Asn Met Asn Trp Val Lys Gln Ser Asn Gly Lys Ser Leu
        50                  55                  60

Glu Trp Ile Gly Val Ile Asn Pro Asn Tyr Gly Thr Ile Arg Tyr Asn
65                  70                  75                  80

Gln Lys Phe Lys Gly Lys Ala Thr Leu Thr Val Asp Gln Ser Ser Ser
            85                  90                  95

Thr Ala Tyr Met Gln Leu Asn Ser Leu Thr Ser Glu Asp Ser Ala Val
            100                 105                 110

Tyr Tyr Cys Ala Gly Leu Leu Arg Gly Tyr Tyr Ala Met Asp Tyr Trp
        115                 120                 125

Gly Gln Gly Thr Ser Val Thr Val Ser Ser
    130                 135
```

ANTIBODY SPECIFICALLY BINDING TO WRS PROTEIN, AND USE THEREOF

TECHNICAL FIELD

This is a United States national phase under 35 USC § 371 of International Patent Application No. PCT/KR2020/009477 filed Jul. 17, 2020, which in turn claims priority under 35 USC § 119 to Korean Patent Application No. 10-2019-0087233, filed on Jul. 18, 2019. The disclosures of all such applications are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "619_SeqListing_ST25.txt" created on Jan. 18, 2022 and is 9,099 bytes in size. The sequence listing contained in this .txt file is part of the specification and is hereby incorporated by reference herein in its entirety.

The present invention relates to an antibody specifically binding to a WRS (tryptophanyl-tRNA synthetase) protein and the use thereof, and more specifically to an antibody or a fragment thereof specifically binding to a polypeptide having the amino acid sequence represented by SEQ ID NO: 2 in a WRS (tryptophanyl-tRNA synthetase) protein, a polynucleotide encoding the antibody, a vector including the polynucleotide, a cell transformed using the vector, and the use thereof.

BACKGROUND ART

Aminoacyl-tRNA synthetase (ARS) is an enzyme that functions to attach a specific amino acid to the corresponding tRNA. Higher organisms are composed of 23 enzymes, including 20 enzymes that depend on the type of amino acid and 3 additional types involved in multisynthetase complex formation such as AIMP1(p43), (AIMP2)p38, and (AIMP3) p18, and besides enzymes participating in multisynthetase complexes, some enzymes exist in free form. Recently, however, it has been reported that ARSs have various other active functions in specific environments, in addition to the basic function thereof, one of which is WRS (tryptophanyl-tRNA synthetase).

WRS was first reported among ARSs secreted from cells and exhibiting cytokine activity, and many papers have been published to date on the potential of WRS as an important biomarker for various types of cancer including colorectal cancer (Ghanipour A. et al. The prognostic significance of tryptophanyl-tRNA synthetase in colorectal cancer (2009) Cancer Epidemiol. Biomarkers Prev. 18(11), 2949-2955). Moreover, it has been reported that the level of WRS may be used as a marker for rapidly and accurately diagnosing infectious diseases and complications thereof in such a manner in which, when an infectious disease caused by bacterial, viral or fungal infection occurs, the level of WRS in the body increases rapidly from the initial stage of infection, and in particular, when an infectious inflammatory disease is contracted, the level of WRS is greatly increased compared to that of a normal person, and in the case of a non-infectious inflammatory disease, the WRS level is not related thereto (Korean Patent Application Publication No. 10-2017-0027313).

These results show that WRS may be present in the sera of patients suffering from cancer and infectious diseases, and that WRS may be used as an important diagnostic biomarker for these diseases.

However, despite the importance of ARSs including WRS as biomarkers, ARSs have many similarities in the protein structure, so antibodies obtained from animal immune responses show cross-reactivity, that is, capability to bind to other ARSs, and there are many cases in which high-sensitivity antibodies are not produced at all.

DISCLOSURE

Technical Problem

Accordingly, the present inventors have conducted thorough research to develop an antibody specifically binding to WRS, and have found that antibodies that specifically bind to a polypeptide including a specific amino acid sequence in the WRS protein and have specific CDR (complementarity-determining region) sequences exhibit very high binding specificity and binding affinity to WRS, and thus the usefulness thereof is very high, thus culminating in the present invention.

Therefore, it is an object of the present invention to provide an antibody or a fragment thereof specifically binding to a polypeptide having the amino acid sequence represented by SEQ ID NO: 2 in a WRS (tryptophanyl-tRNA synthetase) protein.

It is another object of the present invention to provide a polynucleotide encoding the antibody or the fragment thereof, a vector including the polynucleotide, and a cell transformed with the vector.

It is still another object of the present invention to provide a method of producing an antibody or a fragment thereof binding to human WRS including producing a polypeptide including light-chain and heavy-chain variable regions by culturing the cell under conditions in which the polynucleotide is expressed and recovering the polypeptide from the cell or the culture medium in which the cell is cultured.

It is yet another object of the present invention to provide a composition for diagnosing cancer or an infectious disease or infectious complications including the antibody or the fragment thereof.

Also, it is yet another object of the present invention to provide a composition for diagnosing cancer or an infectious disease or infectious complications consisting of the antibody or the fragment thereof.

Also, it is yet another object of the present invention to provide a composition for diagnosing cancer or an infectious disease or infectious complications essentially consisting of the antibody or the fragment thereof.

It is still yet another object of the present invention to provide the use of the antibody or the fragment thereof for the manufacture of an agent for diagnosing cancer.

It is a further object of the present invention to provide a method of diagnosing cancer, including:

a) obtaining a sample from a subject;

b) measuring the WRS protein expression level in the sample using the antibody or the fragment thereof; and c) determining that the subject has cancer when the protein expression level measured in step b) is increased.

It is still a further object of the present invention to provide the use of the antibody or the fragment thereof for the manufacture of an agent for diagnosing an infectious disease or infectious complications.

It is yet a further object of the present invention to provide a method of diagnosing an infectious disease or infectious complications, including:

a) obtaining a sample from a subject;

b) measuring the WRS protein expression level in the sample using the antibody or the fragment thereof; and c) determining that the subject has an infectious disease or infectious complications when the protein expression level measured in step b) is increased.

Technical Solution

In order to accomplish the above object of the present invention, the present invention provides an antibody or a fragment thereof specifically binding to a polypeptide having the amino acid sequence represented by SEQ ID NO: 2 in a WRS (tryptophanyl-tRNA synthetase) protein.

In order to accomplish another object of the present invention, the present invention provides a polynucleotide encoding the antibody or the fragment thereof, a vector including the polynucleotide, and a cell transformed with the vector.

In order to accomplish still another object of the present invention, the present invention provides a method of producing an antibody or a fragment thereof binding to human WRS including producing a polypeptide including light-chain and heavy-chain variable regions by culturing the cell under conditions in which the polynucleotide is expressed and recovering the polypeptide from the cell or the culture medium in which the cell is cultured.

In order to accomplish yet another object of the present invention, the present invention provides a composition for diagnosing cancer or an infectious disease or infectious complications including the antibody or the fragment thereof.

Also, the present invention provides a composition for diagnosing cancer or an infectious disease or infectious complications consisting of the antibody or the fragment thereof.

The present invention provides a composition for diagnosing cancer or an infectious disease or infectious complications essentially consisting of the antibody or the fragment thereof.

In order to accomplish still yet another object of the present invention, the present invention provides the use of the antibody or the fragment thereof for the manufacture of an agent for diagnosing cancer.

In order to accomplish a further object of the present invention, the present invention provides a method of diagnosing cancer, including:

a) obtaining a sample from a subject;

b) measuring the WRS protein expression level in the sample using the antibody or the fragment thereof; and c) determining that the subject has cancer when the protein expression level measured in step b) is increased.

In order to accomplish still a further object of the present invention, the present invention provides the use of the antibody or the fragment thereof for the manufacture of an agent for diagnosing an infectious disease or infectious complications.

In order to accomplish yet a further object of the present invention, the present invention provides a method of diagnosing an infectious disease or infectious complications, including:

a) obtaining a sample from a subject;

b) measuring the WRS protein expression level in the sample using the antibody or the fragment thereof; and c) determining that the subject has an infectious disease or infectious complications when the protein expression level measured in step b) is increased.

Hereinafter, a detailed description will be given of the present invention.

The present invention provides an antibody or a fragment thereof specifically binding to a polypeptide having the amino acid sequence represented by SEQ ID NO: 2 in a WRS (tryptophanyl-tRNA synthetase) protein.

In the present invention, the term 'WRS' refers to tryptophanyl-tRNA synthetase, which is also known as tryptophan-tRNA ligase, TrpRS, WARS, and the like. WRS is an enzyme that mediates aminoacylation between the amino acid tryptophan and tRNA. WRS is encoded by the WARS gene in humans, and the amino acid sequence and mRNA nucleotide sequence of the protein are known under GenBank accession number NP_004175.2 (protein), GenBank accession number NM_004184.3 (mRNA nucleotide sequence), and the like. There are two isoforms of WRS: a cytoplasmic form (WARS or tryptophanyl-tRNA synthetase, cytoplasmic) and a mitochondrial form (WARS2 or tryptophanyl-tRNA synthetase, mitochondrial). WRS in the present invention preferably takes a cytoplasmic form.

In the present invention, the term 'antibody' refers to immunoglobulin (Ig), and is a generic term for proteins that selectively act on antigens and are involved in in-vivo immunity. A whole antibody found in nature generally consists of two pairs of a light chain (LC) and a heavy chain (HC), which are polypeptides consisting of several domains, or these two paired structures of HC/LC are constituted as basic units. There are five types of heavy chains that make up mammalian antibodies, denoted by the Greek letters α, δ, ε, γ, and μ, and, depending on the type of heavy chain, different types of antibodies, such as IgA, IgD, IgE, IgG, and IgM, are formed. There are two types of light chains that make up mammalian antibodies, denoted by λ and κ.

The heavy and light chains of an antibody are structurally divided into a variable region and a constant region depending on the variability of the amino acid sequence. The constant region of the heavy chain includes 3 or 4 heavy-chain constant regions, namely CH1, CH2, and CH3 (IgA, IgD and IgG antibodies) and CH4 (IgE and IgM antibodies) depending on the type of antibody, and the light chain includes CL, which is one constant region. The variable region of each of the heavy and light chains consists of one domain of a heavy-chain variable region (VH) or a light-chain variable region (VL). In each of the light and heavy chains, the variable region and the constant region are aligned side by side and are linked via one covalent disulfide bond, and the heavy chains of two molecules bound to the light chains are linked via two covalent disulfide bonds to form a whole antibody. The whole antibody specifically binds to an antigen through the variable regions of the heavy and light chains, and since the whole antibody includes two pairs of a heavy chain and a light chain (HC/LC), the whole antibody of one molecule has bivalent monospecificity, that is, capability to bind to the same two antigens through two variable regions. The variable region of the antibody that binds to the antigen is called the antigen-binding site of the antibody, and the part recognized by the antibody on the surface of the antigen is called the epitope.

The variable region of an antibody including an antigen-binding site is subdivided into a framework region (FR) having low sequence variability and a complementarity-determining region (CDR), which is a hypervariable region having high sequence variability. In each of the VH and VL, three CDRs and four FRs are arranged in the order of FR1-CDR1-FR2-CDR2-FR3-CDR3-FR4 in the direction from the N-terminus to the C-terminus. The CDR having the highest sequence variability within the variable region of the antibody directly binds to the antigen, and is the most important in determining antigen specificity of the antibody.

In the present invention, the antibody or the fragment thereof is an antibody or a fragment thereof specifically binding to a WRS protein or a variant protein thereof, and specifically binds to a polypeptide including the sequence of 48$^{th}$ to 104$^{th}$ amino acids (SEQ ID NO: 2) of the WRS protein represented by SEQ ID NO: 1.

The 'antibody' of the present invention may also be referred to as an 'anti-WRS antibody', 'humanized anti-WRS antibody', or 'modified humanized anti-WRS antibody', and is used in the broadest sense in the present invention. Particularly, the antibody includes monoclonal antibodies (including full-length monoclonal antibodies), polyclonal antibodies, multispecific antibodies (e.g. bispecific antibodies), and antibody fragments (e.g. variable regions and other sites of the antibody that exhibit the desired bioactivity (e.g. binding to WRS)).

The antibody of the present invention is an antibody in which a specific amino acid sequence is included in the light-chain and heavy-chain CDRs so that the antibody is capable of selectively binding to WRS, and includes both a monoclonal antibody and a polyclonal antibody, preferably a monoclonal antibody. Moreover, the antibody of the present invention includes all of a chimeric antibody, a humanized antibody, and a human antibody, and is preferably a human antibody.

A monoclonal antibody of the present invention is an antibody obtained from a population of substantially homogeneous antibodies, in which the individual antibodies that make up the population are identical except for possible naturally-occurring mutations that may be present in small amounts. The monoclonal antibody binds very specifically to a single epitope.

In the present invention, the term 'monoclonal' refers to the properties of an antibody obtained from a population of substantially homogeneous antibodies, and does not necessarily mean that the antibody must be produced through any particular method. For example, a monoclonal antibody of the present invention may be produced through the hybridoma method first described in Kohler et al. (1975, Nature 256: 495), or through a recombinant DNA method (U.S. Pat. No. 4,816,567). It may also be isolated from phage antibody libraries using, for example, techniques described in the literature (Clackson et al.(1991) Nature 352: 624-628 and Marks et al.(1991) J. Mol. Biol. 222: 581-597 and Presta (2005) J. Allergy Clin. Immunol. 116:731).

The antibody of the present invention particularly includes a chimeric antibody in which a portion of the heavy chain and/or light chain is identical to or homologous to corresponding sequences in antibodies derived from a particular species or belonging to a particular antibody class, while the remaining portion thereof is identical to or homologous to corresponding sequences in antibodies derived from another species or belonging to another antibody class, so long as the antibody of the present invention exhibits the desired bioactivity (e.g. selective binding to NRS) (U.S. Pat. No. 4,816,567 and Morrison et al.(1984) Proc. Natl. Acad. Sci. USA 81: 6851-6855).

A humanized antibody is an antibody including both human and non-human (e.g. mouse, rat) antibody sequences.

In general, other than the region (CDR) binding to the epitope, the remainder belongs to a human antibody, and the region (CDR) binding to the epitope may include a sequence of non-human origin. A fully human antibody is an antibody including only a human immunoglobulin protein sequence, and may be produced from mice, mouse cells, or hybridomas derived from mouse cells, or may be produced through a phage display method.

The antibody or the fragment thereof according to the present invention preferably includes an antibody light-chain variable region (VL) including a complementarity-determining region (CDR) L1 including the amino acid sequence represented by SEQ ID NO: 3, a complementarity-determining region (CDR) L2 including the amino acid sequence represented by SEQ ID NO: 4, and a complementarity-determining region (CDR) L3 including the amino acid sequence represented by SEQ ID NO: 5, and an antibody heavy-chain variable region (VH) including a complementarity-determining region (CDR) H1 including the amino acid sequence represented by SEQ ID NO: 6, a complementarity-determining region (CDR) H2 including the amino acid sequence represented by SEQ ID NO: 7, and a complementarity-determining region (CDR) H3 including the amino acid sequence represented by SEQ ID NO: 8.

In addition, the antibody or the fragment thereof according to the present invention, including the CDRs of the light and heavy chains described above, may include a light-chain variable region (VL) including the amino acid sequence represented by SEQ ID NO: 9 and a heavy-chain variable region (VH) including the amino acid sequence represented by SEQ ID NO: 10.

The antibody or the fragment thereof according to the present invention is not limited with regard to the type thereof, so long as it has the above CDRs, VH and VL, or light and heavy chains, and the antibody may be an IgG, IgA, IgM, IgE, or IgD antibody. Preferably, the antibody is an IgG antibody.

In the present invention, the fragment of the antibody is a fragment of an antibody that maintains WRS-specific binding affinity, and preferably, the fragment has at least 20%, 50%, 70%, 80%, 90%, 95%, 100%, or more of the WRS protein affinity of the parent antibody. Specifically, the fragment may take a form such as Fab, F(ab)2, Fab', F(ab')2, Fv, diabody, scFv, etc.

Fab (fragment antigen-binding) is an antigen-binding fragment of an antibody, and includes one variable domain and one constant domain of each of heavy and light chains. F(ab')2 is a fragment produced by hydrolyzing an antibody with pepsin, and takes a form in which two Fabs are linked through a disulfide bond at a heavy-chain hinge. F(ab') is a monomeric antibody fragment having a form in which a heavy-chain hinge is added to Fab separated by reducing the disulfide bond of the F(ab')2 fragment. Fv (variable fragment) is an antibody fragment including only a variable region of each of the heavy and light chains. ScFv (single-chain variable fragment) is a recombinant antibody fragment in which a heavy-chain variable region (VH) and a light-chain variable region (VL) are linked by a flexible peptide linker. A diabody is a fragment in a form in which VH and VL of scFv are linked by a very short linker and cannot bind to each other but form a dimer by binding to VL and VH, respectively, of another scFv of the same type.

The antibody or the fragment thereof according to the present invention may include a conservative amino acid substitution (referred to as a conservative variant of the antibody) that does not substantially alter the bioactivity thereof.

In addition, the antibody or the fragment thereof according to the present invention as described above may be conjugated to an enzyme, a fluorescent material, a radioactive material, a protein, or the like, but the present invention is not limited thereto. Also, methods of conjugating the above material to the antibody are well known in the art.

The antibody of the present invention may be derived from any animal, including mammals including humans, birds, and the like. Preferably, the antibody is a human, mouse, donkey, sheep, rabbit, goat, guinea pig, camel, horse, or chicken antibody, most preferably a human or mouse antibody.

The hybridoma cells may be produced using a method known in the art. Specifically, the hybridoma cells may be produced by immunizing an animal with a polypeptide having the amino acid sequence of SEQ ID NO: 2 as an immunogen and fusing B cells, which are antibody-producing cells derived from the immunized animal, with myeloma cells to form hybridomas, among which a hybridoma that produces a monoclonal antibody specifically binding to the polypeptide having the amino acid sequence of SEQ ID NO: 2 is then selected. The animal to be immunized may include an animal such as goat, sheep, guinea pig, rat, or rabbit, in addition to a mouse.

A method of immunizing the animal to be immunized may be performed through a method known in the art. For example, a mouse is immunized in a manner in which 1 to 100 μg of the immunogen is emulsified at one time with the same amount of saline and/or an antigen adjuvant such as Freund's adjuvant, and the immunogen is inoculated subcutaneously or intraperitoneally to the abdomen of the animal 2-6 times every 2-5 weeks. After immunization of the animal, the spleen or lymph node is extracted therefrom 3-5 days after final immunization, and the B cells contained in these tissues are fused with myeloma cells in the presence of a fusion promoter according to a cell fusion method known in the art. The fusion promoter that is used may be exemplified by a material such as polyethylene glycol (PEG). Examples of the myeloma cells may include mouse-derived cells such as P3U1, NS-1, P3×63 Ag 8.653, and Sp2/0-Ag14, and rat-derived cells such as AG1 and AG2. In the cell fusion method known in the art, for example, B cells and myeloma cells are mixed at a ratio of 1:1-10:1, and PEG, having a molecular weight of 1,000-6,000, is added thereto at a concentration of 10-80%, followed by culture at 30-37° C. for 1-10 minutes. In addition, the hybridoma producing a monoclonal antibody specifically binding to the polypeptide having the amino acid sequence of SEQ ID NO: 2 may be selected through culture in a selective medium such as a HAT medium or the like in which only hybridoma cells are able to survive and measurement of antibody activity in the hybridoma culture supernatant using a method such as ELISA or the like. Finally, the hybridoma producing a monoclonal antibody specifically binding to the polypeptide having the amino acid sequence of SEQ ID NO: 2 may be selected by repeated cloning through a method such as limiting dilution, etc. on the hybridoma producing a monoclonal antibody specifically binding to the polypeptide having the amino acid sequence of SEQ ID NO: 2.

In addition, the present invention provides a polynucleotide encoding the antibody or the fragment thereof.

In the present invention, the 'polynucleotide' may be an oligonucleotide or nucleic acid, and includes DNA molecules (e.g. cDNA or genomic DNA), RNA molecules (e.g. mRNA), DNA or RNA analogues produced using nucleotide analogues (e.g. peptide nucleic acids and non-naturally occurring nucleotide analogues), and hybrids thereof. The polynucleotide may be single-stranded or double-stranded. The polynucleotide indicates a nucleotide sequence encoding an antibody consisting of heavy and light chains having CDR configurations or VH and VL configurations specific to the polypeptide having the amino acid sequence of SEQ ID NO: 2.

The polynucleotide encoding the antibody or the fragment thereof according to the present invention may be obtained through methods that are well known in the art. For example, it may be synthesized using an oligonucleotide synthesis technique that is well known in the art, such as a polymerase chain reaction (PCR) method, etc., based on the DNA sequence or the corresponding amino acid sequence encoding part or all of the heavy and light chains of the antibody.

In addition, the present invention provides a vector including the polynucleotide.

The 'vector' of the present invention is used for the purpose of replication or expression of the polynucleotide of the present invention for recombinant production of the antibody or the fragment thereof according to the present invention, and generally includes at least one selected from among a signal sequence, an origin of replication, at least one marker gene, an enhancer element, a promoter, and a transcription termination sequence. The vector of the present invention is preferably an expression vector, and more preferably a vector including the polynucleotide of the present invention operably linked to a regulatory sequence, for example, a promoter.

A plasmid, which is a kind of vector, is a linear or circular double-stranded DNA molecule to which external polynucleotide fragments are able to bind. Another form of vector is a viral vector (e.g. replication defective retroviruses, adenoviruses, and adeno-associated viruses), in which additional DNA fragments are introduced into the viral genome. Certain vectors are capable of autonomous replication in the host cell into which they are introduced (e.g. bacterial vectors of bacterial origin and episomal mammalian vectors). Other vectors (e.g. non-episomal mammalian vectors) are integrated into the genome of a host cell through introduction into the host cell, and thereby are replicated along with the host genome.

In the present invention, "vector" may be understood to have the same meaning as "expression vector", which indicates a form of a vector capable of expressing a polynucleotide. A polynucleotide sequence is said to be "operably linked" to a regulatory sequence when the regulatory sequence affects the expression (e.g. level, timing, or location of expression) of the polynucleotide sequence. The regulatory sequence is a sequence that affects the expression (e.g. the level, timing, or location of expression) of a nucleic acid to which it is operably linked. The regulatory sequence may have the effect thereof on the regulated nucleic acid either directly or through the action of one or more other molecules (e.g. polypeptides that bind to the regulatory sequence and/or the nucleic acid). The regulatory sequence includes promoters, enhancers, and other expression control elements. The vector of the present invention preferably includes pOptiVEC™-TOPO and pcDNA™ 3.3-TOPO.

In addition, the present invention provides a cell transformed with the vector.

The cell of the present invention is not particularly limited with regard to the type thereof, so long as it is capable of being used to express the polynucleotide encoding the antibody or the fragment thereof contained in the expression vector of the present invention. Examples of the cell (host cell) transformed with the expression vector according to the invention may include prokaryotes (e.g. *E. coli*), eukaryotes (e.g. yeast or other fungi), plant cells (e.g. tobacco or tomato plant cells), and animal cells (e.g. human cells, monkey cells, hamster cells, rat cells, mouse cells, insect cells, or hybridomas derived therefrom). Preferably, the cell is a cell derived from mammals including humans.

Prokaryotes suitable therefor include gram-negative or gram-positive organisms, for example Enterobacteriaceae, including *Escherichia* such as *E. coli, Enterobacter, Erwinia, Klebsiella, Proteus, Salmonella* such as *Salmonella typhimurium, Serratia* such as *Serratia marcescens, Shigella,* bacilli such as *B. subtilis* and *B. licheniformis, Pseudomonas* such as *P. aeruginosa,* and *Streptomyces.* The cell of the present invention is not particularly limited, so long as it is able to express the vector of the present invention, but is preferably *E. coli.*

As the cell of the present invention, the most common eukaryote example is *Saccharomyces cerevisiae.* However, many other genera, species, and strains may be used, examples of which include, but are not limited to, *Schizosaccharomyces pombe, Kluyveromyces* hosts, such as *K. lactis, K. fragilis* (ATCC 12,424), *K. bulgaricus* (ATCC 16,045), *K. wickerhamii* (ATCC 24,178), *K. waltii* (ATCC 56,500), *K. drosophilarum* (ATCC 36,906), *K. thermotolerans,* and *K. marxianus; Yarrowia* (EP 402,226); *Pichia pastoris* (EP 183,070); *Candida; Trichoderma reesei* (EP 244,234); *Neurospora crassa; Schwanniomyces,* such as *Schwanniomyces occidentalis;* and filamentous fungi, such as *Neurospora, Penicillium, Tolypocladium,* and *Aspergillus* hosts, including *A. nidulans* and *A. niger.*

The term 'transformation' refers to a change in the genotype of a host cell due to the introduction of an exogenous polynucleotide, and indicates the introduction of an exogenous polynucleotide into a host cell regardless of the method used for the transformation. The exogenous polynucleotide introduced into a host cell may be maintained after being integrated into the genome of the host cell, or may be maintained without integration, and the present invention includes both cases.

The recombinant expression vector capable of expressing the antibody or the fragment thereof specifically binding to the WRS protein according to the present invention may be introduced into a cell for producing an antibody or a fragment thereof to thus transform the cell through a method known in the art, examples of which include, but are not limited to, transient transfection, microinjection, transduction, cell fusion, calcium phosphate precipitation, liposome-mediated transfection, DEAE dextran-mediated transfection, polybrene-mediated transfection, electroporation, gene gun, and other known methods for introducing a nucleic acid into a cell.

Moreover, the cell of the present invention is a cultured cell that may be transformed or transfected with the polynucleotide of the present invention or the vector including the same, which may be subsequently expressed in the host cell. A recombinant cell is a cell transformed or transfected with the polynucleotide to be expressed. The cell of the present invention may also be a cell that includes the polynucleotide of the present invention but in which the polynucleotide is not expressed to a desired level unless the regulatory sequence is introduced into the cell such that it is operably linked to the polynucleotide.

The cell of the present invention may be cultured in various media. Commercially available media such as Ham's F10 (Sigma-Aldrich Co., St. Louis, MO), minimum essential medium (MEM, Sigma-Aldrich Co.), RPMI-1640 (Sigma-Aldrich Co.), and Dulbecco's modified Eagle's medium (DMEM, Sigma-Aldrich Co.) are suitable for cell culture. The medium may be supplemented with hormones and/or other growth factors, salts, buffers, nucleotides, antibiotics, trace elements, and glucose or equivalent energy sources, as necessary.

In addition, the present invention provides a method of producing an antibody or a fragment thereof binding to WRS, including producing a polypeptide including light-chain and heavy-chain variable regions by culturing the cell under conditions in which the polynucleotide is expressed and recovering the polypeptide from the cell or the culture medium in which the cell is cultured.

The cell in the production method according to the present invention is as described above, and includes a polynucleotide encoding the antibody of the present invention. The polypeptide in the above production method may be the antibody or the fragment thereof according to the present invention, or may be configured to include the antibody or the fragment thereof according to the present invention and an additional amino acid sequence.

As such, the antibody or the fragment thereof according to the present invention may be recovered using a method that is well known to those skilled in the art. For culture, the culture medium composition and culture conditions may vary depending on the type of cell, and may be appropriately selected and controlled by those skilled in the art.

The antibody molecule may accumulate in the cytoplasm of a cell, may be secreted from the cell, or may be targeted to a periplasm or supernatant by an appropriate signal sequence, and is preferably targeted to the periplasm or supernatant. Moreover, it is preferable to refold the produced antibody molecule using a method that is well known to those skilled in the art and assemble the same into a functional conformation. The polypeptide may be recovered through various methods depending on the properties of the produced polypeptide and the properties of the cell, which may be appropriately selected and controlled by those skilled in the art.

The polypeptide may be produced in a cell or in the periplasmic space, or may be directly secreted into the medium. If the polypeptide is produced in a cell, the cell may be disrupted to thereby release the protein as a first step. Particulate debris, host cells, or lysed fragments are removed through, for example, centrifugation or ultrafiltration. When the antibody is secreted into the medium, the supernatant from the expression system is usually first concentrated using a commercially available protein concentration filter, such as an Amicon or Millipore Pellicon ultrafiltration unit. A protease inhibitor such as PMSF may be included in any preceding step in order to inhibit proteolysis, and antibiotics may be included in order to prevent the growth of adventitious contaminants. The antibody produced from the cell may be purified using, for example, hydroxyapatite chromatography, gel electrophoresis, dialysis, and affinity chromatography, and the antibody of the present invention is preferably purified through affinity chromatography.

Since the antibody or the fragment thereof according to the present invention specifically binds to WRS, it is useful in diagnostic assays for detecting and quantifying a WRS protein, for example detecting WRS expression in a certain cell, tissue, or serum.

Accordingly, the present invention provides a WRS-specific detection method including bringing the antibody or the fragment thereof into contact with a sample and detecting the antibody or the fragment thereof. In order to 'detect' the antibody or the fragment thereof, the antibody or the fragment thereof may typically be labeled with a detectable moiety.

For example, labeling with radioactive isotopes or fluorescent labels may be performed using a technique described in the literature [Current Protocols in Immunology, Volumes 1 and 2, 1991, Coligen et al., Ed. Wiley-Interscience, New York, N. Y., Pubs]. Radioactivity may be measured through, for example, scintillation counting, and fluorescence may be quantified using a fluorometer. Alternatively, various enzyme-substrate labels are available, and examples of enzymatic labels include luciferases such as Drosophila luciferase and bacterial luciferase (U.S. Pat. No. 4,737,456), luciferin, 2,3-dihydrophthalazinediones, malate dehydrogenase, urase, peroxidase such as horseradish peroxidase (HRPO), alkaline phosphatase, β-galactosidase, glucoamylase, lysozyme, saccharide oxidase (e.g. glucose oxidase, galactose oxidase, and glucose-6-phosphate dehydrogenase), heterocyclic oxidase (e.g. uricase and xanthine oxidase), lactoperoxidase, microperoxidase, and the like. Techniques for conjugating enzymes to antibodies are described in, for example, O'Sullivan et al. [1981, Methods for the Preparation of Enzyme-Antibody Conjugates for use in Enzyme Immunoassay, in Methods in Enzym. (J. Langone & H. Van Vunakis, eds.), Academic press, N. Y., 73: 147-166].

The label may be indirectly conjugated to the antibody using a variety of known techniques. For example, the antibody may be conjugated to biotin, and any label falling within the three broad categories mentioned above may be conjugated to avidin, or vice versa. Biotin binds selectively to avidin, so this label may be conjugated to the antibody in an indirect manner. Alternatively, in order to achieve indirect conjugation of a label to the antibody, the antibody may be conjugated with a small hapten (e.g. digoxin), and any one of the different types of labels mentioned above may be conjugated to an anti-hapten antibody (e.g. an anti-digoxin antibody). Thereby, indirect conjugation of the label to the antibody may be achieved.

The antibody or the fragment thereof according to the present invention may be used in any known assay method, such as competitive binding assays, direct and indirect sandwich assays, and immunoprecipitation assays.

The antibody or the fragment thereof according to the present invention may be used for a diagnostic kit, namely a diagnostic kit for performing a diagnostic assay including instructions for use and a packaged combination of reagents in predetermined amounts. When the antibody is labeled with an enzyme, the kit may include a substrate and a cofactor required by the enzyme as a substrate precursor that provides a chromophore or fluorophore. Moreover, other additives, such as stabilizers, buffers (e.g. blocking buffers or lysis buffers), and the like, may be included. The relative amounts of various reagents may be varied widely in order to provide concentrations in the solution of the reagents suitable for optimizing the sensitivity of the assay. The reagents may be provided in the form of a dry powder, usually freeze-dried, including excipients that, upon dissolution, will provide a reagent solution having the appropriate concentration.

WRS detected by the antibody of the present invention was first reported among ARSs secreted from cells and exhibiting cytokine activity, and to date many papers have been published on the potential thereof as an important biomarker in various types of cancer including colorectal cancer (Ghanipour A. et al. The prognostic significance of tryptophanyl-tRNA synthetase in colorectal cancer (2009) Cancer Epidemiol Biomarkers Prev. 18(11), 2949-2955).

Therefore, WRS may be detected and used as a diagnostic marker for the diagnosis of certain types of cancer, progression of disease, and evaluation of prognosis before and after treatment. The diagnosis of cancer and evaluation of prognosis thereof according to the present invention may be performed by detecting the WRS protein in a biosample.

Accordingly, the present invention provides a composition for diagnosing cancer including the antibody or the fragment thereof according to the present invention as an active ingredient.

The type of cancer is not particularly limited, and examples thereof may include breast cancer, colorectal cancer, lung cancer, small cell lung cancer, stomach cancer, liver cancer, blood cancer, bone cancer, pancreatic cancer, skin cancer, head or neck cancer, skin or intraocular melanoma, uterine cancer, ovarian cancer, rectal cancer, anal cancer, colon cancer, breast cancer, fallopian tube carcinoma, endometrial carcinoma, cervical cancer, vaginal cancer, vulvar carcinoma, Hodgkin's disease, esophageal cancer, cancer of the small intestine, endocrine adenocarcinoma, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureter cancer, renal cell carcinoma, renal pelvic carcinoma, CNS tumors, primary CNS lymphoma, spinal cord tumors, brainstem glioma, and pituitary adenoma, preferable examples thereof including colorectal cancer or pancreatic cancer.

Meanwhile, it has been reported that the expression level of WRS increases rapidly from the initial stage of infection upon bacterial, viral or fungal infection, and also that, when symptoms such as pneumonia or sepsis appear as infectious complications, the WRS level is greatly increased compared to normal controls. Furthermore, in sepsis patients, the expression level of WRS has a high correlation with the severity and prognosis of sepsis, and since the WRS level increases only in cases of infectious inflammation, it is possible to quickly and accurately distinguish an infectious inflammatory disease and a non-infectious inflammatory disease from each other, and thus it has very high value as a diagnostic marker for use in the treatment of novel infectious diseases and infectious complications. In particular, the level of WRS in the sera of patients suffering from sepsis or septic shock caused by bacterial or fungal infection is greatly increased compared to the sera of healthy normal controls, and there is no statistically significant difference in the increasing trend of WRS in patients suffering from sepsis caused by gram-negative bacteria, gram-positive bacteria, or fungal infection, so WRS may be useful for diagnosing sepsis caused by all of gram-negative bacteria, gram-positive bacteria, and fungal infection. In particular, it is known that there is no statistically significant difference in the level of WRS in the sera of patients suffering from autoimmune diseases, such as systemic inflammation reactive symptom (SIRS), non-infectious chronic inflammatory diseases such as asthma and rheumatoid arthritis, and Sjogren's syndrome, compared to normal controls. Therefore, the expression level of WRS does not increase in all inflammatory responses, but increases specifically only in inflammatory responses induced by bacterial, viral or fungal infection. Moreover, the level of WRS is increased more in septic shock patients than in sepsis patients, so the expression level of WRS is also associated with the severity of sepsis. It may be determined that the higher the expression level of WRS, the more severe the sepsis symptoms (Korean Patent Application Publication No. 10-2017-0027313). By detecting the expression level of WRS in a biosample, it is possible to diagnose an infectious disease or infectious complications and predict the prognosis thereof.

Accordingly, the present invention provides a composition for diagnosing an infectious disease or infectious complications including the antibody or the fragment thereof according to the present invention as an active ingredient.

The biosample includes blood and other liquid samples of biological origin, biopsy samples, solid tissue samples such as tissue cultures, or cells derived therefrom. More specific examples thereof may include, but are not limited to, a tissue, extract, cell lysate, whole blood, plasma, serum, saliva, ocular fluid, cerebrospinal fluid, sweat, urine, milk, ascitic fluid, synovial fluid, peritoneal fluid, and the like. The sample may be obtained from a subject. The subject includes an animal, preferably a mammal, most preferably a human. Pretreatment of the sample may be performed before use for detection. Examples thereof may include filtration, distillation, extraction, concentration, inactivation of interfering components, addition of reagents, and the like. Also, nucleic acids and proteins may be isolated from the sample and used for detection.

The detection is as described above.

In the present invention, infection means that one or more types of exogenous bacteria (all bacteria, including gram-negative and gram-positive bacteria), viruses, and fungi enter the body and settle, multiply, and parasitize. The infectious disease may be any disease that occurs by causing a reaction in the living body as a result of infection by a pathogen. Reactions of the infectious disease may include inflammation, pain, fever, fatigue, edema, reduced blood pressure, and the like. Preferably, the infectious disease of the present invention includes salmonellosis, food poisoning, typhoid fever, paratyphoid fever, pneumonia, pulmonary tuberculosis, tuberculosis, sepsis, septic shock, urinary tract infection, cystitis, pyelonephritis, urethritis, prostatitis, upper respiratory tract infection, and otitis media, more preferably salmonellosis, food poisoning, pneumonia, sepsis, and septic shock, and most preferably sepsis or septic shock.

In the present invention, sepsis is a systemic inflammatory reaction syndrome that appears as a complication of an infectious disease. In cases in which the cause of sepsis cannot be early diagnosed promptly and accurately, sepsis is a fatal disease that causes death due to progression to severe sepsis or septic shock, multiple organ dysfunction syndrome (MODS), which leads to dysfunction of the lungs, kidneys, liver, circulatory system, etc., disseminated intravascular coagulation syndrome (DIC), acute respiratory urgency syndrome (ARDS), or acute renal failure (AKI).

Sepsis as used herein includes, but is not limited to, sepsis associated with the final stages of sepsis, severe sepsis, septic shock, and complications of sepsis, such as multiple organ dysfunction syndrome (MODS), disseminated intravascular coagulation syndrome (DIC), acute respiratory urgency syndrome (ARDS), or acute renal failure (AKI), and includes any stage of sepsis.

In addition, the present invention provides the use of the antibody or the fragment thereof for the manufacture of an agent for diagnosing cancer.

In addition, the present invention provides a method of diagnosing cancer, including:
   a) obtaining a sample from a subject;
   b) measuring the WRS protein expression level in the sample using the antibody or the fragment thereof; and
   c) determining that the subject has cancer when the protein expression level measured in step b) is increased.

In one embodiment, the present invention provides a method of diagnosing and treating cancer in a subject (to be tested), including:
   i) obtaining a sample from a subject;
   ii) measuring the expression level of the WRS protein in the sample;
   iii) determining that the subject has cancer when the protein measured in step ii) is completely expressed; and
   iv) treating cancer by subjecting the subject of the determination to administration of a therapeutic drug (an anticancer drug, etc.) for treating cancer, radiotherapy, or surgery.

The methods including steps i) to iv) are to be understood based on the method including steps a) to c) described above.

Step iv) is performing treatment of the disease by subjecting the subject diagnosed with the disease in step iii) to administration of a therapeutic drug such as an anticancer drug, radiotherapy, or surgery.

In addition, the present invention provides the use of the antibody or the fragment thereof for the manufacture of an agent for diagnosing an infectious disease or infectious complications.

In addition, the present invention provides a method of diagnosing an infectious disease or infectious complications, including:
   a) obtaining a sample from a subject;
   b) measuring the WRS protein expression level in the sample using the antibody or the fragment thereof; and
   c) determining that the subject has an infectious disease or infectious complications when the protein expression level measured in step b) is increased.

In one embodiment, the present invention provides a method of diagnosing and treating an infectious disease or infectious complications in a subject (to be tested), including:
   i) obtaining a sample from a subject;
   ii) measuring the expression level of the WRS protein in the sample;
   iii) determining that the subject has an infectious disease or infectious complications when the protein measured in step ii) is completely expressed; and
   iv) treating the infectious disease or infectious complications by subjecting the subject of the determination to administration of a therapeutic drug for treating an infectious disease or infectious complications or surgery.

The methods including steps i) to iv) are to be understood based on the method including steps a) to c) described above.

Step iv) is performing treatment of the disease by subjecting the subject diagnosed with the disease in step iii) to administration of a therapeutic drug, surgery, or the like.

The 'treatment' of the present invention refers generically to ameliorating cancer or symptoms of cancer or an infectious disease or infectious complications or symptoms thereof, and may include eliminating, substantially preventing, or ameliorating the condition of the disease and alleviating, eliminating, or preventing one symptom or most symptoms resulting from the disease, but the present invention is not limited thereto.

In the present invention, the term 'comprising' or 'including' is used synonymously with 'containing' or 'characterized by', and means that, in the composition or method, additional constituent elements or method steps not mentioned are not excluded. The term 'consisting of' excludes additional elements, steps, or constituents that are not mentioned. The term 'essentially consisting of' means, in the scope of the composition or method, including the described constituent elements or steps as well as constituent elements or steps that do not substantially affect the basic properties thereof.

Advantageous Effects

The antibody or the fragment thereof according to the present invention specifically binds to WRS and has no cross-reactivity with other proteins included in the same ARS family, so WRS detection and inhibition are possible. The antibody or the fragment thereof according to the present invention can be effectively used for detecting WRS and diagnosing WRS-related diseases such as cancer, inflammatory diseases, or infectious diseases.

DESCRIPTION OF DRAWINGS

FIG. 1 shows the amino acid sequences of the light-chain and heavy-chain variable regions of the monoclonal antibody specifically binding to WRS selected in the present invention and nucleotide sequences encoding the same;

FIG. 2 shows results confirming approximate molecular weights and band positions through electrophoresis after construction of the WRS protein (1-471) represented by the amino acid sequence of SEQ ID NO: 1 and fragment peptides thereof (48-471, 1-104, 1-154, and 48-154);

FIG. 3 shows the results of detection of the WRS protein (1-471) and fragment peptides thereof (48-471, 1-104, 1-154, and 48-154) through Western blotting using the antibody of the present invention in order to identify the polypeptide sequence in WRS specifically recognized by the monoclonal antibody produced in Example of the present invention;

FIG. 4 schematically shows the polypeptide in WRS specifically recognized by the monoclonal antibody produced in Example of the present invention based on the results of Western blotting confirmed in the experimental results of FIG. 3;

FIG. 5 shows the results of a comparison of WRS-binding specificity in the monoclonal antibody produced in Example of the present invention and two commercial antibodies; and FIG. 6 shows the results of indirect ELISA assay on cross-reactivity of the monoclonal antibody produced in Example of the present invention.

MODE FOR INVENTION

A better understanding of the present invention may be obtained through the following examples. These examples are merely set forth to illustrate the present invention, and are not to be construed as limiting the scope of the present invention.

Example 1

Production of Monoclonal Antibody (1) Production of Hybridoma Cell
1) Animal Immunization and Cell Fusion
    Preparation of immunogen: 1.5 to 2 mg of WRS protein (purity >75%, concentration >0.4 mg/ml)
    Animal immunization: Antibody production was induced by inoculating the immunogen into Balb/c mice.

Cell fusion: At least 10,000 hybridoma cells were obtained by electro-fusion of mouse B cells and mouse myeloma cells.
2) Selection of Hybridoma Cell
    Primary selection: Hybridoma cells producing an antigen-binding antibody were selected through indirect ELISA.
    Secondary selection: One hybridoma cell line binding to an antigen was selected through Western blotting using the positive clones obtained in the primary selection, and the antibody produced from the selected hybridoma cell line was named 4D10G6.
    Isotyping: Five clones having the best results in the selection process were subjected to isotyping.
3) Subcloning, Cell Expansion, Freezing Storage, and Antibody Production
    Subcloning, cell expansion, and freezing storage: Clones having good results were subjected to subcloning, cell expansion, and freezing storage.
    Antibody production: An antibody was produced in an amount of at least 2 mg from the hybridoma cell line having the best results in the selection process.
2. Formation of Ascites
    1) After adaptation of mice for at least 3 days, a pristane adjuvant was administered in an amount of 100 pl/mouse thereto. The hybridoma cell line was cultured so that it could be injected 5 to 7 days after administration of the pristane adjuvant.
    2) The cultured hybridoma cell line was collected in a 50 ml tube, washed three times with 10 ml PBS, and centrifuged.
    3) After centrifugation, the supernatant was removed by suction, after which the number of cells required per 100 μl was calculated, added with 1× PBS, mixed well, and then transferred into a 1.5 ml tube.
    4) The above solution was placed in a 1 ml syringe, and the air in the syringe was removed by turning the syringe needle upwards.
    5) 100 μl of the solution was injected intraperitoneally to each Balb/c mouse, after which the mice were placed in a cage, and whether ascites was present was observed.
    6) From 5 days after injection of the hybridoma cell line into the mice, abdominal bloating was observed every day.
    7) When abdominal bloating was noted, ascites fluid was collected from the abdominal cavity of the mice using a product with an injection needle of 23 G or less (using a 3 ml or 5 ml syringe).
    8) The ascites fluid, collected and placed in a tube, was incubated at RT for 10 min to allow red blood cells to aggregate, followed by centrifugation.
    9) After centrifugation, only the supernatant was placed in a new 1.5 ml tube and stored at −70° C.
3. Production of Antibody
    1) The produced ascites fluid was taken out at −70° C. and thawed at 4° C., and the type of beads to be used was determined by confirming the subtype of the antibody to be purified. The amount of beads used was 0.5 the volume of ascites fluid.
    2) Well-mixed Protein A beads or G beads were placed in the calculated amount in a 5 ml chromatography column, and bead washing was performed by allowing 5 ml of 1× PBS to flow into the column.
    3) After completion of washing, the thawed ascites fluid was placed in the column, and the column was capped.
    4) Rotation binding was performed at 4° C. for 1 hr so that the beads and the antibody were bound to each other.

5) After rotation binding, the entire solution was subjected to a flow-through process.

6) Column washing was performed using 100 ml of 1× PBS.

7) 100 µl of a neutralization buffer was added to a 1.5 ml tube, and 1 ml of an IgG elution buffer was added to the column to enable neutralization immediately after IgG elution. A total of 10 fractions were obtained under the same conditions.

8) A portion of each fraction was loaded on a 12% SDS-PAGE gel, and the band was confirmed through gel staining. During staining, fractions were stored at 4° C.

9) The fractions having distinct bands were collected, placed in dialysis tubing, and sealed with a clip to prevent leakage. The dialysis tubing and a stirrer bar were placed in a beaker containing 1 L of 1× PBS, and dialysis was performed at 4° C. for 1 hr using a stirrer.

10) Dialysis was performed using 1 L of fresh 1× PBS overnight (15 hr) under the same conditions as in 9) above.

11) The next day, the solution was collected from the dialysis tubing and immediately quantified using a BCA assay kit.

Example 2

Sequencing

Total RNA was isolated from the hybridoma cells according to the technical manual of a TRIzol reagent. Total RNA was reverse-transcribed into cDNA using universal primers according to the technical manual for a PrimeScript 1st Strand cDNA Synthesis Kit. The antibody fragments of a heavy-chain variable region (VH) and a light-chain variable region (VL) were amplified through RACD (rapid amplification of cDNA ends). The amplified antibody fragment was cloned separately into a standard cloning vector. Colony PCR was performed to screen clones having inserts of the correct size. At least 5 colonies having inserts of the correct size were sequenced for each fragment. The sequences of the different clones were aligned, and consensus sequences of these clones were provided.

The light-chain and heavy-chain variable region amino acid sequences of the sequenced monoclonal antibody of the present invention and the sequences of polynucleotide encoding the same are illustrated in FIG. 1.

Example 3

Identification of Polypeptide in WRS to Which Monoclonal Antibody Specifically Binds In order to identify the polypeptide region recognized by the monoclonal antibody produced in Example 1, the WRS protein (1-471) of SEQ ID NO: 1 consisting of 471 amino acids and the protein fragments (48-471, 1-104, 1-154, and 45-154) were prepared.

1) In order to purify the recombinant WRS protein and fragment peptides thereof, competent cells for protein expression were transformed with the plasmid in which the WRS protein and fragment genes thereof were cloned into a pET28a vector.

2) The transformed cells were spread on an LB (+Kanamycin) plate, followed by culture at 37° C. for 15 hr.

3) The next day, a single colony was inoculated into 3 ml of LB (+Kan), followed by culture at 200 rpm and 37° C. for 3 hr.

4) All of the small cultured cells were placed in 500 ml of LB (+Kan), followed by culture at 37° C. and 200 rpm for 4 hr.

5) When 0.8<OD value<1 was measured, 250 µl of a 1 M IPTG stock was added thereto (final 0.5 mM IPTG), followed by induction at 18° C. and 200 rpm overnight (15 hr).

6) The next day, the induction-treated cells were centrifuged at 4,000 rpm for 10 min.

7) The supernatant was removed, and the pellets were suspended in 10 ml of washing buffer 1.

8) The cells were lysed using a sonicator. Treatment with 35% AMPL for 2 sec and storage on ice for min were performed. This process was repeated 14 times (a total of 15 sonications).

9) Centrifugation was performed at 15,000 rpm and 4° C. for 30 min to separate pellets and the supernatant from each other.

10) 200 µl of Ni-NTA beads were placed in poly-prep chromatography columns, and 5 ml of washing buffer 1 was added to reach equilibrium.

11) After centrifugation, the supernatant was filtered using a 0.45 µm filter in a 50 ml tube and was allowed to flow into the column containing the beads. This procedure was performed once more.

12) Washing was performed using washing buffer 1.

13) Washing was performed using washing buffer 2.

14) Washing was performed using washing buffer 3.

15) Washing was performed using washing buffer 4.

16) The washed column was placed on a 1.5 ml tube and an elution buffer was then passed therethrough, and thus an eluate was collected.

17) A 5× sample buffer and DW were placed in a 5 ml tube and subjected to a flow-through process, and a washing buffer and the eluate were added thereto and then boiled in a heat block for 5 min.

18) A premade 15-well comb and 15% SDS-PAGE gel were assembled in a cassette, the cassette was placed in the tank, and the gel and the tank were filled with a 1× running buffer.

19) The protein marker and sample were sequentially loaded.

20) During gel loading, dialysis tubing was heated in a DW bath at 100° C. for 10 min. The DW was replaced with fresh DW and the heating process in a DW bath was repeated twice more, followed by cooling using 200 ml of cold 1× PBS.

21) After loading, the gel was separated from the cassette, and staining was performed by pouring instant blue until the gel was submerged (FIG. 2).

Western blotting was performed according to a typical method using the WRS protein produced through the above method, fragments thereof, and the monoclonal antibody produced in Example 1 as the primary antibody.

As a result, as shown in FIG. 3, the monoclonal antibody was confirmed to specifically recognize a fragment (SEQ ID NO: 2) consisting of $48^{th}$ to $104^{th}$ amino acids among 1-471 amino acids of the WRS protein consisting of the amino acid sequence of SEQ ID NO: 1.

Example 4

Analysis of Binding Affinity of Antibody

In order to evaluate binding affinity of the monoclonal antibody produced in Example 1 and two commercial antibodies (Abnova, anti-WRS antibody (Cat #H00007453-M02) and Novus biological, anti-WRS antibody (Cat NBP2-32186)), indirect ELISA assay was performed on the full-length WRS protein of SEQ ID NO: 1.

Briefly, the binding affinity of the antibodies was evaluated according to the following method.

1) The WRS protein was diluted to 1 μg/ml in PBS, loaded in an amount of 100 μl/well into a 96-well plate, and reacted at room temperature for 1 hr, whereby the wells were coated therewith.

2) After completion of coating, washing was performed once with a PBST (0.05% Tween-20) buffer, and 3% BSA and PBST (0.1% tween-20) were dispensed, followed by a blocking reaction at room temperature for 1 hr.

3) The biotin-attached antibody was diluted with a blocking buffer according to each concentration and then reacted at room temperature for 1 hr.

4) Washing was performed with PBST (0.05% Tween-20).

5) Streptavidin-HRP was diluted with a blocking buffer, followed by reaction at room temperature for 1 hr.

6) Washing was performed five times with PBST (0.05% Tween-20) to remove all unattached residue.

7) 50 μl/well of TMB was added thereto, followed by reaction at room temperature for 5 min, after which the same amount of 2 M $H_2SO_4$ was added to terminate the reaction.

8) Absorbance was measured using a spectrophotometer (Sunrise, Tecan) (450 nm).

9) The $EC_{50}$ values were calculated from the results of 8) above.

The results thereof are shown in Table 1 below.

TABLE 1

|          | 4D10G6 | Abnova | Novus |
|----------|--------|--------|-------|
| $EC_{50}$ | 40.5   | 1655.6 | 532.8 |

As is apparent from Table 1, it was confirmed that the antibody according to the present invention exhibited very high affinity to the WRS protein compared to the two commercial antibodies.

Example 5

Analysis of Binding Specificity of Antibody

In order to evaluate the binding specificity of the monoclonal antibody produced in Example 1 and two commercial antibodies (Abnova, anti-WRS antibody (Cat #H00007453-M02) and Novus biological, anti-WRS antibody (Cat #NBP2-32186)), 20 μg of an HCT116 cell lysate was treated with each of a primary antibody and a secondary antibody under the following conditions, and Western blotting was performed according to a typical method.

Primary antibody (room temperature, 1 hr)
4D10G6: 1 μg/ml
Abnova Ab: 1:5,000 dilution
Novus Ab: 1:10,000 dilution Secondary antibody (room temperature, 1 hr)
Anti-mouse HRP (Millipore, AP181P): 1:10,000 dilution: Abnova, 4D10G6
Anti-rabbit HRP (Millipore, AP187P): 1:10,000 dilution: Novus The results thereof are shown in FIG. 5.

As shown in FIG. 5, it was confirmed that the antibody according to the present invention showed a single band, whereas several bands appeared in the two commercial antibodies.

Therefore, it was confirmed that the antibody according to the present invention exhibited very high binding specificity compared to the commercial antibodies.

Example 6

Validation of Cross-Reactivity

In order to evaluate whether the monoclonal antibody produced in Example 1 exhibit cross-reactivity with CRS (cysteinyl-tRNA synthetase), AIMP1 (aminoacyl tRNA synthase complex-interacting multifunctional protein 1), GRS (glycyl tRNA synthetase), and KRS (lysyl tRNA synthetase), which are other ARS (aminoacyl-tRNA synthetase) proteins secreted from the cells, in addition to WRS, indirect ELISA assay was performed according to the following method.

1) Antigen coating: 1 μg/ml in PBS, 100 μl/well, 4° C., overnight coating

2) Washing: 0.05% PBST (0.05% Tween 20), 200 μl/well, 3 times

3) Blocking: 0.5% BSA in 0.05% PBST, 200 μl/well, RT, 1 hr

4) Primary antibody binding: 500 ng/ml in 0.05% PBST, 100 μl/well, RT, 1 hr

5) Secondary antibody binding: anti-mouse HRP (AP160P) 1:10,000 in 0.05% PBST, 100 μl/well, RT, 1 hr 6) TMB detection 7) Reaction termination (2 M $H_2SO_4$)

8) Absorbance measurement: 450 nm

The results thereof are shown in FIG. 6.

As shown in FIG. 6, it was confirmed that the antibody according to the present invention did not bind to ARS proteins other than WRS.

INDUSTRIAL APPLICABILITY

The antibody or the fragment thereof according to the present invention specifically binds to WRS and has no cross-reactivity with other proteins included in the same ARS family, making it possible to detect and inhibit WRS, and can thus be effectively used for detecting WRS and diagnosing WRS-related diseases such as cancer, inflammatory diseases, or infectious diseases, thereby exhibiting high industrial applicability.

The invention claimed is:

1. An antibody or antigen binding fragment thereof which specifically binds to a polypeptide comprising the amino acid sequence of SEQ ID NO: 2 in a WRS (tryptophanyl-tRNA synthetase) protein, the antibody or antigen binding fragment thereof comprising a light-chain variable region (VL) comprising a complementarity determining region (CDR) L1 comprising the amino acid sequence of SEQ ID NO: 3, a complementarity-determining region (CDR) L2 comprising the amino acid sequence of SEQ ID NO: 4, and a complementarity-determining region (CDR) L3 comprising the amino acid sequence of SEQ ID NO: 5, and a heavy-chain variable region (VH) comprising a complementarity-determining region (CDR) H1 comprising the amino acid sequence of SEQ ID NO: 6, a complementarity-determining region (CDR) H2 comprising the amino acid sequence of SEQ ID NO: 7, and a complementarity-determining region (CDR) H3 comprising the amino acid sequence of SEQ ID NO: 8.

2. The antibody or the fragment thereof according to claim 1, wherein the antibody or the fragment thereof comprises a light-chain variable region comprising an amino acid sequence represented by SEQ ID NO: 9 and a heavy-chain variable region comprising an amino acid sequence represented by SEQ ID NO: 10.

3. The antibody or the fragment thereof according to claim 1, wherein the antibody is a monoclonal antibody.

4. The antibody or the fragment thereof according to claim 1, wherein the antibody is selected from the group consisting of IgG, IgA, IgM, IgE, and IgD.

5. The antibody or the fragment thereof according to claim 1, wherein the fragment of the antibody is selected from the group consisting of diabody, Fab, Fab', F(ab)2, F(ab')2, Fv, and scFv.

6. A composition comprising:

an antibody or antigen binding fragment thereof which specifically binds to a polypeptide comprising the amino acid sequence of SEQ ID NO: 2 in a WRS (tryptophanyl-tRNA synthetase) protein, the antibody or antigen binding fragment thereof comprising a light-chain variable region (VL) comprising a complementarity determining region (CDR) L1 comprising the amino acid sequence of SEQ ID NO: 3, a complementarity-determining region (CDR) L2 comprising the amino acid sequence of SEQ ID NO: 4, and a complementarity-determining region (CDR) L3 comprising the amino acid sequence of SEQ ID NO: 5, and a heavy-chain variable region (VH) comprising a complementarity-determining region (CDR) H1 comprising the amino acid sequence of SEQ ID NO: 6, a complementarity-determining region (CDR) H2 comprising the amino acid sequence of SEQ ID NO: 7, and a complementarity-determining region (CDR) H3 comprising the amino acid sequence of SEQ ID NO: 8; and an excipient.

7. A method of detecting WRS protein in a sample, comprising:

a) Obtaining the sample from a subject;

b) Contacting the sample with an antibody or antigen binding fragment thereof, wherein the antibody or antigen binding fragment thereof is labeled with a detectable moiety; and c) Detecting WRS protein in the sample by detecting a signal from the detectable moiety;

wherein the antibody or antigen binding fragment thereof specifically binds to a polypeptide comprising the amino acid sequence of SEQ ID NO: 2 in a WRS (tryptophanyl-tRNA synthetase) protein, and wherein the antibody or antigen binding fragment thereof comprises a light-chain variable region (VL) comprising a complementarity determining region (CDR) L1 comprising the amino acid sequence of SEQ ID NO: 3, a complementarity-determining region (CDR) L2 comprising the amino acid sequence of SEQ ID NO: 4, and a complementarity-determining region (CDR) L3 comprising the amino acid sequence of SEQ ID NO: 5, and a heavy-chain variable region (VH) comprising a complementarity-determining region (CDR) H1 comprising the amino acid sequence of SEQ ID NO: 6, a complementarity-determining region (CDR) H2 comprising the amino acid sequence of SEQ ID NO: 7, and a complementarity-determining region (CDR) H3 comprising the amino acid sequence of SEQ ID NO: 8.

* * * * *